(12) United States Patent
Kanikanti et al.

(10) Patent No.: US 10,543,170 B2
(45) Date of Patent: Jan. 28, 2020

(54) TABLETS WITH IMPROVED ACCEPTANCE AND GOOD STORAGE STABILITY

(71) Applicant: BAYER ANIMAL HEALTH GMBH, Leverkusen (DE)

(72) Inventors: Venkata-Rangarao Kanikanti, Leverkusen (DE); Hans-Juergen Hamann, Dormagen (DE); Georg Schulte, Wuppertal (DE); Patrick Billian, Leverkusen (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 14/653,676

(22) PCT Filed: Dec. 17, 2013

(86) PCT No.: PCT/EP2013/076878
§ 371 (c)(1),
(2) Date: Jun. 18, 2015

(87) PCT Pub. No.: WO2014/095845
PCT Pub. Date: Jun. 26, 2014

(65) Prior Publication Data
US 2015/0342889 A1 Dec. 3, 2015

(30) Foreign Application Priority Data

Dec. 19, 2012 (EP) .................................... 12198101

(51) Int. Cl.
| | | |
|---|---|---|
| *A61K 31/27* | (2006.01) | |
| *A61K 31/4985* | (2006.01) | |
| *A61K 31/506* | (2006.01) | |
| *A61K 9/00* | (2006.01) | |
| *A61K 9/20* | (2006.01) | |

(52) U.S. Cl.
CPC .......... *A61K 9/0056* (2013.01); *A61K 9/2018* (2013.01); *A61K 9/2054* (2013.01); *A61K 9/2059* (2013.01); *A61K 9/2095* (2013.01); *A61K 31/27* (2013.01); *A61K 31/4985* (2013.01); *A61K 31/506* (2013.01)

(58) Field of Classification Search
CPC .. A61K 9/2058; A61K 9/2054; A61K 9/2018; A61K 31/216; A61K 31/4965; A61K 31/506; A61K 9/2059
See application file for complete search history.

(56) References Cited

U.S. PATENT DOCUMENTS

| | | | |
|---|---|---|---|
| 4,382,892 A | 5/1983 | Hayakawa et al. | |
| 4,472,405 A | 9/1984 | Stern | |
| 4,670,444 A | 6/1987 | Grohe et al. | |
| 4,704,459 A | 11/1987 | Todo et al. | |
| 4,730,000 A | 3/1988 | Chu | |
| 4,861,779 A | 8/1989 | Jefson et al. | |
| 6,159,932 A | 12/2000 | Mencke et al. | |
| 7,348,027 B2 | 3/2008 | Rose et al. | |
| 8,628,794 B2 | 1/2014 | Isele | |
| 2005/0203097 A1 | 9/2005 | Folger et al. | |
| 2006/0222684 A1* | 10/2006 | Isele | A61K 9/0056 424/442 |
| 2013/0203692 A1* | 8/2013 | Soll | A61K 45/06 514/30 |
| 2017/0208851 A1* | 7/2017 | Kerwood | A23L 33/40 |

FOREIGN PATENT DOCUMENTS

| | | |
|---|---|---|
| DE | 102008022520 A1 | 11/2009 |
| EP | 279343 A2 | 8/1988 |
| EP | 1457213 | 9/2004 |
| EP | 2080515 A1 | 7/2009 |
| GB | 2475701 A * | 6/2011 |
| JP | 09-509669 | 9/1997 |
| JP | 2004-269534 | 9/2004 |
| JP | 2007-500004 | 1/2007 |
| RU | 2356534 | 12/2010 |
| WO | 1995/020942 A1 | 8/1995 |
| WO | WO-95/23594 | 9/1995 |
| WO | 2005/000275 A1 | 7/1997 |
| WO | WO-2005/013714 | 2/2005 |
| WO | 2010132286 A1 | 11/2010 |
| WO | 2012049156 A1 | 4/2012 |

\* cited by examiner

*Primary Examiner* — James D. Anderson
(74) *Attorney, Agent, or Firm* — McBee Moore & Vanik IP LLC

(57) ABSTRACT

The present invention relates to tablets for animals, having improved acceptance and good storage stability.

18 Claims, 1 Drawing Sheet

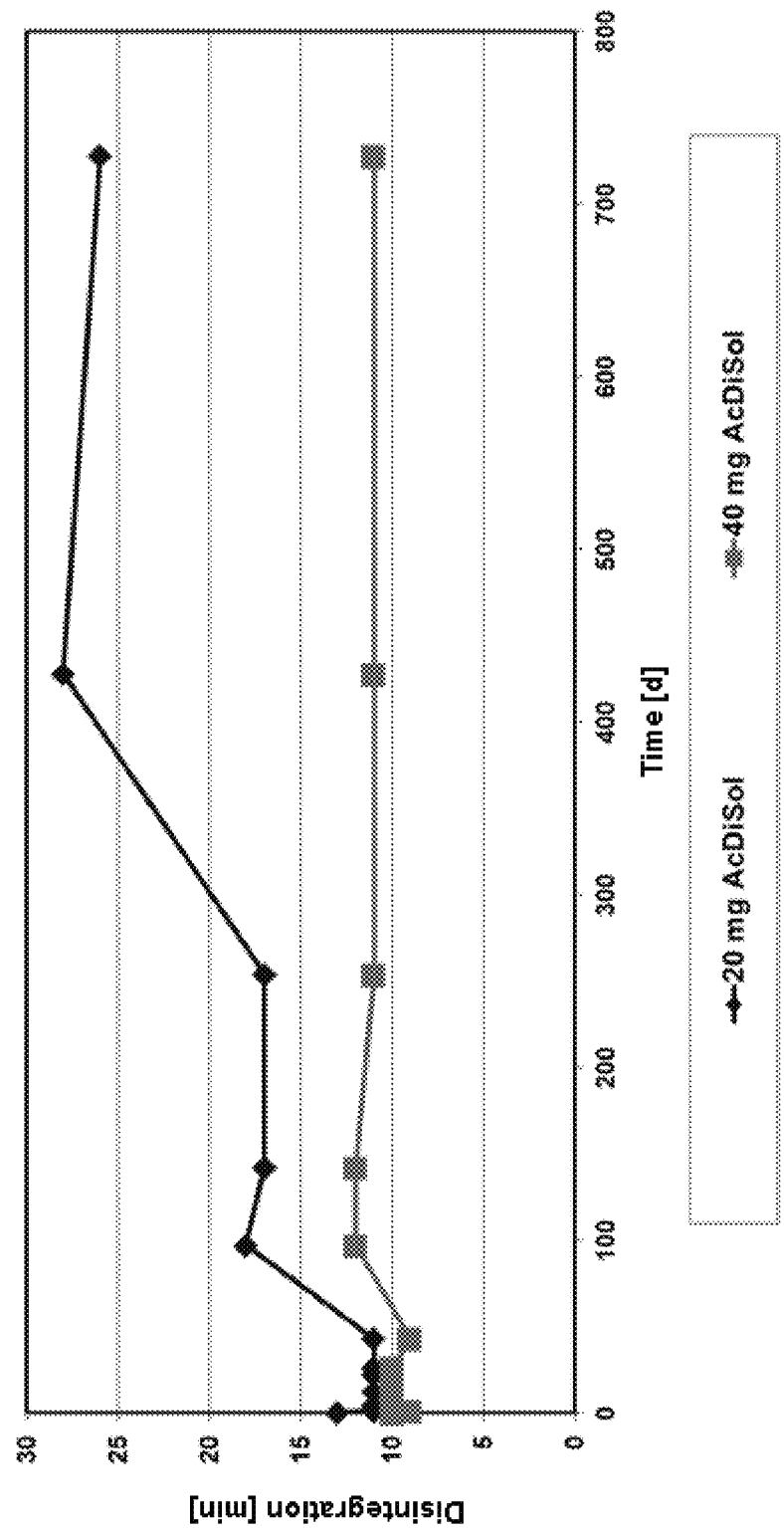

TABLETS WITH IMPROVED ACCEPTANCE AND GOOD STORAGE STABILITY

The present invention relates to tablets for animals, having improved acceptance and good storage stability.

Administering tablets to animals is problematic because the animals do not find them attractive at all and generally receive them only involuntarily. Typically, tablets have to be packed into feed so that they can be administered. In this connection, it is not always guaranteed that the drug can be administered in full and thus in the right dose. The release profile of the medicament can also change during administration in feed.

EP279343 already discloses active-ingredient combinations composed of phenylguanidines or benzimidazoles and tetrahydropyrimidines and also formulations thereof.

WO 2005/000275 describes tablets containing enrofloxacin and taste substances or flavouring substances.

WO 2012/049156 discloses starch-free chewable formulations ("chewables") containing flavouring substances.

WO 95/20942 describes attractive bait for animals—especially for dogs—into which medicaments can be introduced and thus administered.

Chewable tablets used for administering anxiolytics to domesticated animals are described in WO 2010/132286.

As shown, for example, by some of the above-mentioned documents, it is already known in principle that palatability can be increased by addition of appropriate flavourings and/or taste substances. However, as a result of said addition, the properties of tablets are frequently impaired to an extent that is not acceptable in practice. For example, tablets having a high proportion of meat flavouring have a tendency to alter their properties during storage. This is due in particular to the ageing of the meat flavouring. Owing to the ageing processes of the meat flavouring, the disintegration time of the tablets, for example, can be altered to an extent that is not acceptable for medicaments. In the case of tablets which do not contain any meat flavouring, it is generally not difficult to attain a good storage stability. However, the use of meat flavouring in such tablets entails the difficulties discussed above.

There is therefore a need for highly palatable tablets which satisfy the requirements for medicaments and in particular have a good storage stability.

The invention provides a tablet containing:
at least one active pharmaceutical ingredient,
at least 28% by weight of meat flavouring and
at least 2% by weight of a stabilizing agent.

In a further embodiment, the invention provides:
tablets containing:
at least one active pharmaceutical ingredient,
at least 30% by weight of meat flavouring,
from 3 to 8% by weight of a stabilizing agent.

According to the invention, the tablets contain at least one active ingredient. The active ingredients can in principle be all possible active ingredients which are typically orally administered to animals.

The active ingredients encompass, for example, those against parasites (ectoparasites and/or endoparasites), such as acaricidal, insecticidal, anthelmintic active ingredients; antimicrobial active ingredients, such as antiviral, antibiotic active ingredients and those effective against protozoa, such as Coccidia; in addition, for example anti-inflammatory and psychotropic active ingredients and also proton pump inhibitors, etc.

Examples of suitable active ingredients are the following known classes: acaricides, such as the macrocycles abamectin, doramectin, eprinomectin, ivermectin, milbemectin, nikkomycins, selamectin, tetranactin and thuringiensin; bridged diphenyl acaricides such as azobenzene, benzoximate, benzyl benzoate, bromopropylate, chlorbenside, chlorfenethol, chlorfenson, chlorfensulphide, chlorobenzilate, chloropropylate, dicofol, diphenyl sulphone, dofenapyn, fenson, fentrifanil, fluorbenside, proclonol, tetradifon and tetrasul; carbamate acaricides such as benomyl, carbanolate, carbaryl, carbofuran, fenothiocarb, methiocarb, metolcarb, promacyl and propoxur; oxime carbamate acaricides such as aldicarb, butocarboxim, oxamyl, thiocarboxim and thiofanox; dinitrophenol acaricides such as binapacryl, dinex, dinobuton, dinocap, dinocap-4, dinocap-6, dinocton, dinopenton, dinosulfon, dinoterbon and DNOC; formamidine acaricides such as amitraz, chlordimeform, chloromebuform, formetanate and formparanate; growth regulators for mites such as clofentezine, dofenapyn, fluazuron, flubenzimine, flucycloxuron, flufenoxuron and hexythiazox; organochlorine acaricides such as bromocyclen, camphechlor, dienochlor and endosulfan; pyrazole acaricides such as acetoprole, fipronil and analogues and derivatives thereof, tebufenpyrad, pyriprole and vaniliprole; pyrethroid acaricides such as, for example, pyrethroid ester acaricides such as acrinathrin, bifenthrin, cyhalothrin, cypermethrin, alpha-cypermethrin, fenpropathrin, fenvalerate, flucythrinate, flumethrin, fluvalinate, tau-fluvalinate and permethrin, pyrethroid ether acaricides such as halfenprox; quinoxaline acaricides such as quinomethionate and thioquinox; sulphite ester acaricides such as propargite; tetronic acid acaricides such as spirodiclofen; and acaricides not belonging to a particular class, such as acequinocyl, amidoflumet, arsenic oxide, chlormethiuron, closantel, crotamiton, diafenthiuron, dichlofluanid, disulfiram, fenazaflor, fenazaquin, fenpyroximate, fluacrypyrim, fluenetil, mesulfen, mnaf, nifluridide, pyridaben, pyrimidifen, sulfiram, sulfluramid, sulphur and triarathene.

Insecticides may belong to various chemical classes, such as, for example, chlorinated hydrocarbons, organophosphates, carbamates, pyrethroids, formamidines, borates, phenylpyrazoles and macrocyclic lactones. Known insecticides include imidacloprid, fenthion, fipronil, allethrin, resmethrin, fenvalerate, permethrin, malathion and derivatives thereof. According to one embodiment, insecticides of the neonicotinoid class are preferred, for example acetamiprid, clothianidin, dinotefuran, imidacloprid (see above), nitenpyram, thiacloprid and thiamethoxam. Frequently used growth-regulating active ingredients (insect growth regulators, IGRs) are, for example, benzoylphenyl ureas, such as diflubenzuron, lufenuron, noviflumuron, hexaflumuron, triflumuron and teflubenzuron or active ingredients such as fenoxycarb, pyriproxyfen, methoprene, kinoprene, hydroprene, cyromazine, buprofezin, pymetrozine and derivatives thereof.

Anthelmintics may be endoparasiticides or endectocides and encompass the following well-known groups: macrocyclic lactones, benzimidazoles, probenzimidazoles, imidazothiazoles, tetrahydropyrimidines, organophosphates, piperazines, salicylanilides and cyclic depsipeptides (see below).

Preferred anthelmintics encompass macrocyclic lactones having a broad spectrum, such as avermectins, milbemycins and derivatives thereof, such as, for example, ivermectin, doramectin, moxidectin, selamectin, emamectin, eprinomectin, milbemectin, abamectin, milbemycin oxime, nemadectin and derivatives thereof. The classes of the benzimidazoles, benzimidazole carbamates and probenzimidazoles also encompass active compounds, such as thiabendazole, mebendazole, fenbendazole, oxfendazole, oxibendazole, albendazole, luxabendazole, netobimin, parbendazole, flubendazole, cyclobendazole, febantel, thiophanate and derivatives thereof. Imidazothiazoles encompass active compounds such as tetramisole, levamisole and derivatives thereof. The tetrahydropyrimidines encompass active compounds such as morantel, pyrantel and derivatives thereof. Organophosphates encompass active compounds such as dichlorvos, haloxon, trichlorfon and derivatives thereof. Salicylanilides encompass active compounds such as closantel, tribromsalan, dibromsalan, oxyclozanide, clioxanide, rafoxanide, brotianide, bromoxanide and derivatives thereof. Cyclic depsipeptides encompass compounds having 6 to 30 ring atoms and are composed of amino acids and hydroxycarboxylic acids as structural units of the ring; examples include PF 1022A, emodepside and others which are described in U.S. Pat. No. 6,159,932, to which reference is hereby expressly made.

Antimicrobial compounds are, for example, various penicillins, tetracyclines, sulphonamides, cephalosporins, cephamycin, aminoglycosides, trimethoprim, dimetridazole, erythromycin, framycetin, furazolidone, various pleuromutilins such as tiamulin, valnemulin, various macrolides, streptomycin, clopidol, salinomycin, monensin, halofuginone, narasin, robenidine, quinolones, etc. Quinolones, preferably fluoroquinolones, encompass compounds which are described in U.S. Pat. Nos. 4,670,444; 4,472,405; 4,730,000; 4,861,779; 4,382,892; and 4,704,459, to which reference is expressly made. Specific examples of fluoroquinolones include benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, perfloxacin, temafloxacin, tosufloxacin, sarafloxacin and sparfloxacin. A further example of an antibacterial fluoroquinolone which can be used in animals is pradofloxacin. Specific examples of other quinolones include pipemidic acid and nalidixic acid.

Apart from the above-mentioned active pharmaceutical ingredients, it is also possible to have vitamins or minerals, for example, as constituents.

The active ingredients may preferably be, for example, depsipeptides selected from the group consisting of PF 1022A and emodepside.

Preferred antimicrobial fluoroquinolones are in particular enrofloxacin or pradofloxacin.

In a particularly preferred embodiment, the tablets according to the invention contain an active ingredient selected from febantel, pyrantel (typically in the form of a salt, the embonate being preferred) and praziquantel or a two-part combination composed of said active ingredients. Even more preferably, febantel, pyrantel embonate and praziquantel are used as a three-part combination in the tablets according to the invention.

The active ingredients can also—where applicable—be used in the form of their salts with pharmaceutically acceptable acids or bases or else as solvates, more particularly hydrates, of the active ingredients or their salts.

Prodrugs of the active ingredients can also be used.

According to the invention, the tablets contain at least one active ingredient in a pharmaceutically effective amount, "pharmaceutically effective amount" meaning a non-toxic amount of active ingredient which can bring about the desired effect. The amount of active ingredient used depends on the active ingredient, the animal treated and on the nature, severity and stage of the disease.

In general, the tablets contain about from 0.0001 to 50% by weight of active ingredient(s). The tablets can contain from 0.01 to 40% by weight, from 0.1 to 35% by weight, from 1 to 30% by weight, from 5 to 30% by weight or from 10 to 30% by weight of active ingredient(s). In further embodiments, the tablets can also contain from 1 to 35% by weight, from 5 to 35% by weight or from 10 to 35% by weight of active ingredient(s).

The amount of active ingredient can also be specified as weight per tablet, for example at least 5 mg, at least 10 mg, at least 20 mg, at least 30 mg, at least 40 mg, at least 50 mg, or at least 100 mg of active ingredient(s). For example, the tablets can contain from 5 to 2000 mg, from 10 to 1500 mg, from 10 to 1000 mg, from 10 to 500 mg, from 20 to 2000 mg, from 20 to 1500 mg, from 20 to 1000 mg, from 20 to 500 mg, from 50 to 2000 mg, from 50 to 1500 mg, from 50 to 1000 mg or from 50 to 500 mg of active ingredient(s).

Febantel is preferably used in concentrations of from 9 to 20% by weight, preferably from 11 to 17% by weight, particularly preferably from 12 to 16% by weight.

Praziquantel is preferably used in concentrations of from 1 to 10% by weight, preferably from 2 to 8% by weight, particularly preferably from 3 to 7% by weight.

Pyrantel, more particularly its embonate, is preferably used in concentrations of from 8 to 20% by weight, preferably from 9 to 17% by weight, particularly preferably from 11 to 15% by weight.

The tablets according to the invention contain meat flavouring. Meat flavouring refers to an additive which is of synthetic or animal origin or a mixture of the two and imparts a meat-like odour and/or taste to the tablets. Preferably, meat flavourings purely of animal origin are used. These are, for example, prepared from beef, poultry, fish, animal skins or animal livers. Preference is given to so-called desiccated liver powders, for example from cattle, sheep, poultry or pig and particularly preferably from poultry or pig.

The meat flavouring is preferably used in an amount of at least 28% by weight, preferably at least 30% by weight, particularly preferably at least 31% by weight. Typically, not more than 40% by weight of meat flavouring, preferably from 30 to 35% by weight, are used (as elsewhere, percentages here are percent by weight of the finished tablets, unless otherwise indicated).

Optionally, it is additionally possible to use flavour enhancers such as, for example, yeast, yeast extracts or glutamate in customary amounts, for example in concentrations of from 1 to 30% by weight, preferably from 1 to 20% by weight.

Furthermore, the tablets according to the invention contain a stabilizing agent. This is to be understood here to mean an excipient which improves the shelf life of the tablets. As already explained, the stabilizing agent is required especially in view of the high proportion of meat flavouring. Its aim is especially to prevent or reduce the ageing processes which occur in connection with the high proportions of meat flavouring. Water-soluble components having a certain action as disintegrant have been found to be useful. Examples of possible stabilizing agents are: sugar alcohols, such as xylitol, mannitol or sorbitol; hydrophilic excipients, such as polyethylene glycol, cross-linked polyvinylpyrrolidone; cellulose derivatives such as methylcellulose, hydroxypropylcellulose (HPC, more particularly low-substituted, "L-HPC"), hydroxypropylmethylcellulose (HPMC); pregelatinized starch, polyvinylcaprolactam-polyvinyl acetate-polyethylene glycol graft copolymer, sodium starch glycolate and croscarmellose sodium. The preferred stabilizing agent is croscarmellose sodium. The tablets according to the invention contain the stabilizing agent in a proportion of at least 2% by weight, typically from 2 to 15% by weight, preferably from 2 to 10% by weight, particularly preferably from 3 to 9% by weight. In one embodiment, relatively low amounts such as from 3 to 8% by weight are already sufficient.

The tablets according to the invention can contain further excipients:

Preferably, the tablets according to the invention contain starch or a starch derivative as filler, which also acts to a certain extent as a disintegrant. Starch can, for example, be starch from wheat, rice, corn, tapioca, rye, oats or potatoes. Modified starches can be physically pretreated starches such as precooked starch or chemically altered starches such as hydroxyethyl starch, hydroxypropyl starch, methyl starch, carboxymethyl starch, starch acetate, hydroxypropyl starch acetate, hydroxyethyl starch acetate, starch phosphates, starch sulphates, or chemically or ionically cross-linked starches such as distarch phosphates, phosphates of hydroxypropylated starches, starch dicarboxylic diesters or salts of anionic starch derivatives. Preferably, starch, such as corn starch for example, is present as filler, specifically in amounts of typically from 5 to 30% by weight, preferably from 8 to 20% by weight, particularly preferably from 10 to 15% by weight, based on the total tablet weight.

The tablets according to the invention further contain a further filler, such as microcrystalline cellulose, maltodextrin; a sugar such as sucrose, glucose or lactose; inorganic fillers, such as calcium carbonate, dicalcium phosphate or magnesium carbonate. Preference is given to using microcrystalline cellulose or more particularly lactose. Lactose is a commercially available pharmaceutical excipient which is available in various forms, for example spray-dried or as anhydrous lactose. According to the invention, preference is given to using lactose monohydrate (e.g. milk sugar, fine from DMV International). The tablets according to the invention contain from 5 to 20% by weight of lactose, preferably from 6 to 15% by weight, particularly preferably from 8 to 12% by weight, based on the total tablet weight.

The tablets according to the invention preferably contain microcrystalline cellulose or a comparable excipient. Microcrystalline cellulose is a commercially available pharmaceutical excipient (e.g. Avicel® PH 101 from FMC). The tablets according to the invention contain from 2 to 10% by weight, preferably from 5 to 10% by weight, particularly preferably from 5.5 to 8% by weight, based on the total tablet weight. In an alternative embodiment, the tablets contain preferably from 3 to 8% by weight and particularly preferably from 4 to 6% by weight, based on the total tablet weight.

The tablets according to the invention may preferably contain silicon dioxide, more particularly colloidal anhydrous silicon dioxide, in amounts of from 0.01 to 0.3% by weight, more particularly from 0.05 to 0.2% by weight, based on the total tablet weight.

The tablets can contain further customary pharmaceutical excipients. Examples of these are: lubricants and glidants such as, for example, magnesium stearate, stearic acid, talc, bentonites; binders such as, for example, starch, gelatin, cellulose ether or linear polyvinylpyrrolidone and also dry binders such as microcrystalline cellulose.

Preferably, the tablets according to the invention contain a lubricant, more particularly magnesium stearate, in amounts of from 0.1 to 1.0% by weight, preferably from 0.1 to 0.5% by weight, based on the total tablet weight.

Furthermore, the tablets according to the invention can contain a binder, such as povidone for example. Povidone refers to hydrophilic polyvinylpyrrolidone polymers, those with a K-value of 30 or less preferably being used as binder. Povidone is used in concentrations of from 0.5 to 5% by weight, preferably from 1 to 3% by weight.

Furthermore, the tablets according to the invention can contain sodium lauryl sulphate or a comparable excipient. Sodium lauryl sulphate is used in concentrations of from 0.05 to 1% by weight, preferably from 0.1 to 0.3% by weight.

If this is required for further therapeutic activities, a further active ingredient can be added to the tablet. If said active ingredient should not be compatible with other ingredients of the tablet, its granules can be applied or introduced as a separate layer. In this way, a 2-layer tablet can be prepared.

Furthermore, the tablet according to the invention can contain at least one antioxidant in order to avoid the oxidation of the active ingredients. Examples of antioxidants are butylhydroxyltoluene (BHT) and propyl gallate.

The tablets according to the invention can be prepared according to a method in which
    (a) the active ingredient(s), and any further excipients, is/are mixed, granulated, and the granules ground if necessary,
    (b) the meat flavouring and any further excipients are added to the mixture from (a) and everything is processed to form a homogeneous compressible mixture, and
    (c) the mixture is subsequently processed to form tablets.

In a further embodiment, the tablets according to the invention can be prepared according to a method in which
    (a) the active ingredient(s), and any further excipients, is/are mixed, granulated, and the granules screened if necessary,
    (b) the meat flavouring is homogenously mixed and dry granulated possibly with further excipients,
    (c) any further excipients are added to the mixture from (a) and (b) and everything is processed to form a homogeneous compressible mixture, and
    (d) the mixture is subsequently processed to form tablets.

Preparation steps (a) can be carried out as wet granulation. Alternatively, preparation steps (a) can be carried out as dry granulation; the missing components are then processed in a separate wet granulation procedure. It is also possible for all components to be dry granulated with croscarmellose sodium in one step. Thereafter, mixing is carried out with, for example, magnesium stearate and colloidal silicon dioxide to obtain a compressible mixture.

The tablets according to the invention are used for simple administration of orally administratable active pharmaceutical ingredients. Therefore, the medicaments according to the invention are suited to the prophylaxis and treatment of corresponding diseases, and in a preferred embodiment they are used in controlling endoparasites, more particularly helminths, in animals. The compositions according to the invention are generally suited to use in animal husbandry and animal breeding in the case of farm animals, breeding animals, zoo animals, laboratory animals, research animals and pets. Preferably, they are used in animals in which it is to be expected that the meat flavouring additive improves palatability. These are typically meat eaters.

The farm animals and breeding animals include mammals such as, for example, cattle, horses, sheep, pigs, goats, camels, water buffalos, donkeys, rabbits, fallow deer, reindeer, fur-bearing animals, such as, for example, minks, chinchilla, racoon.

Laboratory animals and research animals include, for example, mice, rats, guinea pigs, golden hamsters, dogs and cats.

The pets include, for example, dogs and cats.

The compositions according to the invention are particularly preferably used in dogs and cats, more particularly dogs.

The tablets according to the invention are notable for excellent palatability. The mechanical properties of the tablets are good. The use according to the invention of a stabilizing agent also resulted in making the tablets sufficiently storage-stable. Tablets containing no stabilizing agent or an excessively low proportion thereof exhibit a change in disintegration kinetics during storage: the disintegration times of these tablets not in accordance with the invention increase markedly, whereas largely constant disintegration times over a storage period of at least one year, generally even two years, preferably over 3 years, can be achieved with the tablets according to the invention. This is achieved by the addition according to the invention of stabilizing agents which can prevent, in the presence of the high proportions of meat flavouring, the ageing process which occurs. In case of doubt, disintegration times are determined in accordance with "disintegration method 2.9.1 (Test B)" of *European Pharmacopoeia* 6, where permissible tolerances for the disintegration times are also specified.

EXAMPLES

| Ingredients | (1) mg | (2) mg | (3) mg | (4) mg | (5) mg | (6) mg |
|---|---|---|---|---|---|---|
| Febantel | 150.0 | 525.0 | 150.0 | 525.0 | 450.0 | 375.0 |
| Praziquantel | 50.0 | 175.0 | 50.0 | 175.0 | 150.0 | 125.0 |
| Pyrantel embonate | 144.0 | 504.0 | 144.0 | 504.0 | 432.0 | 360.0 |
| Lactose monohydrate | 100.0 | 350.0 | 100.0 | 350.0 | 300 | 250.0 |
| Corn starch | 143.0 | 500.5 | 143.0 | 500.5 | 429.0 | 357.5 |
| Povidone 25 | 18.00 | 63.0 | 18.00 | 63.0 | 54.0 | 45.0 |
| Sodium lauryl sulphate | 2.0 | 7.0 | 2.0 | 7.0 | 6.0 | 5.0 |
| Spray-dried liver powder | 355.4 | 1243.9 | 355.4 | 1243.9 | 1066.2 | 888.5 |
| Microcrystalline cellulose | 49.0 | 171.5 | 49.0 | 171.5 | 147.0 | 122.5 |
| Croscarmellose sodium | 40.0 | 280.0 | 50.0 | 250.0 | 240.0 | 200.0 |
| Magnesium stearate | 3.0 | 10.5 | 3.0 | 10.5 | 9.0 | 7.5 |
| Anhydrous colloidal silicon dioxide | 1.0 | 3.5 | 1.0 | 3.5 | 3.0 | 2.5 |
| Tablet weight | 1055.4 | 3833.9 | 1065.4 | 3803.9 | 3286.2 | 2738.5 |

Method of Preparation:

1st Preparation Step ("Preblend")

Praziquantel, febantel and pyrantel embonate and also some of the corn starch and lactose monohydrate are mixed in a mixer granulator. The mixture is granulated with an aqueous solution of povidone and sodium lauryl sulphate, subsequently dried and carefully screened.

2nd Preparation Step ("Postblend")

Meat flavouring, the rest of the corn starch, and the microcrystalline cellulose are dry mixed, compacted and screened.

Preferably, the meat flavouring has in this connection a moisture content of at least 5.5% (determined by Karl Fischer titration). This gives granules having an acceptable flow behaviour. This is because meat flavouring is hygroscopic and does not flow well as a result. The use of a wet granulation procedure is less preferred, since the flavouring in this case loses its volatile components during the drying step.

3rd Preparation Step ("Final Blend" and Compression)

The required amounts of preblend and postblend are mixed with croscarmellose sodium, magnesium stearate and anhydrous silicon dioxide. This final blend is then processed to form tablets.

Alternatively, preparation step 1 can be carried out as dry granulation.

Instead of preparation step 1 and 2, the components of these two steps can also be dry granulated with the croscarmellose sodium in one step and be mixed with magnesium stearate and anhydrous silicon dioxide.

Long-Term Test of Disintegration Properties

FIG. 1 shows the change in disintegration times during a stress test at 40° C. of formulations containing different amounts of croscarmellose sodium (AcDiSol). For the data labelled as "40 mg AcDiSol" (40 mg of croscarmellose sodium), bone-shaped tablets of the composition according to Example 1 were prepared. In the comparative example, the composition was maintained apart from the lower amount of 20 mg of croscarmellose sodium ("20 mg AcDiSol"). The tablets were stored at 40° C. over the period indicated in days ("Time [d]"); the disintegration properties were checked from time to time. The results are shown in FIG. 1.

It is apparent here that the tablets containing 20 mg of croscarmellose sodium (AcDiSol) exhibit, after about 100 days, a distinctly increased disintegration time, which increases even more strongly within a period of over a year. In contrast, the disintegration time of the tablets containing 40 mg of croscarmellose sodium ("40 mg AcDiSol") remains substantially constant over the entire period of examination. Since a longer disintegration time in the present case is, inter alia, associated with an altered, in this case delayed, release of the active ingredient and consequently an altogether altered profile of action with respect to the tablet originally prepared, such an increase or deviation is distinctly disadvantageous. This disadvantage is eliminated by the accordingly improved storage stability owing to the increased content of stabilizing agent, in this case with a content of 40 mg of croscarmellose sodium for example. With respect to Example 1, the amount of 20 mg of croscarmellose sodium (AcDiSol) corresponds to a content of less than 2% by weight, based on the total tablet weight.

The invention claimed is:

1. A tablet comprising:
   30 to 50% by weight of a combination of febantel, praziquantel, and pyrantel;
   30 to 35% by weight of animal-derived meat flavouring, wherein the meat flavouring is not synthetic;
   3 to 8% by weight of croscarmellose sodium; and
   10 to 15% by weight starch or a starch derivative,
   wherein the starch derivative is selected from the group consisting of precooked starch, hydroxyethyl starch, hydroxypropyl starch, methyl starch carboxymethyl starch, starch acetate, hydroxypropyl starch acetate, hydroxyethyl starch acetate, starch phosphates, starch sulphates, distarch phosphates, phosphates of hydroxypropylated starches, starch dicarboxylic diesters, salts of anionic starch derivatives, and any combination thereof, wherein the tablet has a constant disintegration time over a storage period of at least one year as determined by Method 2.9.1 Disintegration of tablets and capsules, Test B, European Pharmacopoeia 6.0.

2. The tablet according to claim 1, comprising 32 to 33% by weight of the animal-derived meat flavouring.

3. The tablet according to claim 2, comprising about 7% by weight of croscarmellose sodium.

4. The tablet according to claim 1, further comprising 8 to 12% lactose.

5. The tablet according to claim 1, wherein pyrantel is in the form of pyrantel embonate.

6. The tablet according to claim 1, wherein the starch or starch derivative is from wheat, rice, corn, tapioca, rye, oats, potatoes or any combination thereof.

7. The tablet according to claim 6, wherein the starch is corn starch.

8. The tablet according to claim 1, wherein the starch or starch derivative is the starch derivative.

9. The tablet of claim 1, comprising 12 to 16% by weight febantel, 3 to 7% by weight praziquantel, and 11 to 15% by weight pyrantel.

10. The tablet of claim 9, comprising 13 to 14% by weight febantel, 4 to 5% by weight praziquantel, 13 to 14% by weight pyrantel, about 13% by weight of the starch or the starch derivative, 3.5 to 7.5% by weight of croscarmellose sodium, and 32 to 34% by weight of the meat flavouring.

11. The tablet according to claim 10, wherein the starch is corn starch.

12. The tablet according to claim 11, wherein the meat flavouring is spray-dried liver powder.

13. The tablet according to claim 12, further comprising about 9% by weight lactose monohydrate.

14. A tablet comprising 13 to 14% by weight febantel, 4 to 5% by weight praziquantel, 13 to 14% by weight pyrantel, about 13% by weight corn starch, 3.5 to 7.5% by weight croscarmellose sodium, 32 to 34% by weight spray-dried liver powder, about 9% lactose monohydrate, 1 to 3% by weight povidone, 0.1 to 0.3% by weight sodium lauryl sulphate, 4 to 7% by weight microcrystalline cellulose, 0.1 to 0.5% by weight magnesium stearate, and 0.05 to 0.1% by weight colloidal anhydrous silicon dioxide.

15. A method for preparing the tablet according to claim 1, comprising
(a) mixing and granulating the febantel, praziquantel, pyrantel and optionally—any further excipients,
(b) mixing and dry granulating the animal-derived meat flavouring and optionally, further excipients, with the mixture from (a) to produce a homogenous mixture,
(c) adding any further excipients to the mixture produced in (b) to form a homogeneous compressible mixture, and
(d) processing the homogeneous compressible mixture into tablets.

16. A method for preparing the tablet according to claim 1 comprising
(a) mixing a first mixture comprising the febantel, praziquantel, pyrantel, and the starch or starch derivative,
(b) mixing a second mixture comprising the animal-derived meat flavouring and the starch or starch derivative,
(c) mixing the croscarmellose sodium with the first mixture from (a) and the second mixture from (b) to form a homogeneous compressible mixture,
(d) processing the homogeneous compressible mixture to form the tablet.

17. The method according to claim 16, thither comprising adding other excipients in (c).

18. A method for controlling helminths in an animal, comprising administering the tablet of claim 1 to an animal in need thereof.

* * * * *